United States Patent
Visram et al.

(10) Patent No.: US 7,270,662 B2
(45) Date of Patent: Sep. 18, 2007

(54) SURGICAL PERFORATION DEVICE WITH ELECTROCARDIOGRAM (ECG) MONITORING ABILITY AND METHOD OF USING ECG TO POSITION A SURGICAL PERFORATION DEVICE

(76) Inventors: Naheed Visram, 2 Buttonfield Rd., Markham, ON (CA) L3R 9E9; Krishan Shah, 5102 Durie Rd., Mississauga, ON (CA) L5M 2C7

( * ) Notice: Subject to any disclaimer, the term of this patent is extended or adjusted under 35 U.S.C. 154(b) by 176 days.

(21) Appl. No.: 10/760,479

(22) Filed: Jan. 21, 2004

(65) Prior Publication Data
US 2005/0159738 A1    Jul. 21, 2005

(51) Int. Cl.
*A61B 18/18* (2006.01)
(52) U.S. Cl. .......................... 606/41; 128/898
(58) Field of Classification Search ............ 606/27–52; 128/898
See application file for complete search history.

(56) References Cited

U.S. PATENT DOCUMENTS

| | | | |
|---|---|---|---|
| 4,641,649 | A | 2/1987 | Walinsky et al. |
| 4,682,596 | A | 7/1987 | Bales et al. |
| 4,892,104 | A | 1/1990 | Ito et al. |
| 4,936,281 | A | 6/1990 | Stasz |
| 5,098,431 | A | 3/1992 | Rydell |
| 5,364,393 | A | 11/1994 | Auth et al. |
| 5,403,338 | A | 4/1995 | Milo |
| 5,571,088 | A | 11/1996 | Lennox et al. |
| 5,575,772 | A | 11/1996 | Lennox |
| 5,683,366 | A | 11/1997 | Eggers et al. |
| 5,741,249 | A | 4/1998 | Moss et al. |
| 5,893,848 | A | 4/1999 | Negus et al. |
| 5,893,885 | A | 4/1999 | Webster, Jr. |
| 5,904,679 | A | 5/1999 | Clayman |
| 6,032,674 | A | * 3/2000 | Eggers et al. ............... 128/898 |

(Continued)

FOREIGN PATENT DOCUMENTS

EP        0315730        5/1989

(Continued)

OTHER PUBLICATIONS

T. Szili-Torok, G.P. Kimman, D. Theuns, J. Res, J.R.T.C. Roelandt, L.J. Jordaens. "Transseptal Left Heart Catheterisation Guided by Intracardiac Echocardiography". Heart 2001; 86: e11.

(Continued)

*Primary Examiner*—Michael Peffley
*Assistant Examiner*—Pete Vrettakos

(57) ABSTRACT

A device with a functional tip containing at least one active electrode capable of creating a controlled perforation in body tissue through the application of energy (e.g. Radio Frequency (RF)) is described. The position of the tip of the device can be determined in response to ECG measured at the tip and determined by a monitor coupled to the device. The device is useful to remove or perforate unwanted tissue in a controlled manner in any location in the body, particularly in the atrial septum for controlled transseptal puncture. In this application, the device is introduced into the right atrium, and the functional tip is then positioned against the atrial septum. ECG is used to locate the region of the fossa ovalis on the atrial septum. Energy is applied to create the perforation and ECG is monitored to determine if the perforation was created in a desired location.

13 Claims, 8 Drawing Sheets

U.S. PATENT DOCUMENTS

| | | | |
|---|---|---|---|
| 6,093,185 | A | 7/2000 | Ellis et al. |
| 6,117,131 | A | 9/2000 | Taylor |
| 6,171,305 | B1 | 1/2001 | Sherman |
| 6,293,945 | B1 | 9/2001 | Parins et al. |
| 6,296,615 | B1 | 10/2001 | Brockway et al. |
| 6,565,562 | B1 * | 5/2003 | Shah et al. ............... 606/41 |
| 6,650,923 | B1 * | 11/2003 | Lesh et al. ............ 600/407 |
| 6,651,672 | B2 * | 11/2003 | Roth ..................... 128/898 |
| 6,811,544 | B2 | 11/2004 | Schaer |
| 6,814,733 | B2 | 11/2004 | Schwartz et al. |
| 7,029,470 | B2 | 4/2006 | Francischelli et al. |
| 2001/0021867 | A1 | 9/2001 | Kordis et al. |
| 2002/0123749 | A1 | 9/2002 | Jain |
| 2002/0169377 | A1 | 11/2002 | Khairkhahan |
| 2004/0133113 | A1 * | 7/2004 | Krishnan ............... 600/508 |

FOREIGN PATENT DOCUMENTS

| | | |
|---|---|---|
| EP | 1169976 A1 | 1/2002 |
| WO | WO93/20747 | 10/1993 |
| WO | WO 02/058780 A1 | 8/2002 |
| WO | WO 2004/039433 A2 | 10/2003 |
| WO | WO 2004/026134 A1 | 4/2004 |

OTHER PUBLICATIONS

Hector Biddogia, Juan P. Maciel, Jose A. Alvarez et al. "Transseptal Left Heart Catheterization: Usefulness of the Intracavitary Electrocardiogram in the Localization of the *Fossa ovalis*". Catheterization and Cardiovascular Diagnosis 24: 221-225 (1991).

C.R. Conti. "Transseptal Left Heart Catheterization for Radiofrequency Ablation of Accessory Pathways". Clin. Cardiol. 16, 367-368 (1993).

Henri Justino, Lee N. Benson, David G. Nykanen. "Transcatheter Creation of an Atrial Septal Defect Using Radiofrequency Perforation". Catheterization and Cardiovascular Interventions; 54: 83-87 (2001).

Lee N. Benson, David Nykanen, Amanda Collison. "Radiofrequency Perforation in the Treatment of Congenital Heart Disease". Catheterization and Cardiovascular Interventions. 56: 72-82 (2002).

Gideon J. Du Marchie Sarvaas, Kalyani R. Trivedi, Lisa K. Hornberger, K. Jin Lee, Hoel A. Kirsh, Lee N. Benson. "Radiofrequency-Assisted Atrial Septoplasty for an Intact Atrial Septum in Complex Congenital Heart Disease". Catheterization and Cardiovascular Interventions; 56: 412-415 (2002).

N. Shimko, P. Savard, K. Shah. "Radio frequency perforation of cardiac tissue: modelling and experimental results". Med. Biol. Eng. Comput. 38: 575-582 (2000).

Tony Abdel-Massih, Younes Boudjemline, Phillipp Bonhoeffer, Unusual interventional management in an adult with tetralogy of Fallot, Cardiol Young Apr. 2003;13(2):203-5.

Hugh Calkins, Yoon-Nyun Kim, Steve Schmaltz, Joao Sousa, Rafel El-Atassi, Angel Leon, Alan Kadish, Jonathan J. Langberg, Fred Morady; Electrogram Criteria for Identification of Appropriate Target Sites for Radiofrequency Catheter Ablation of Accessory Atrioventricular Connections; Feb. 1992;85(2):565-73.

Tilman Humpl, Bjorn Soderberg, Brian W. McCrindle, David G. Nykanen, Robert M. Freedom, William G. Williams, Lee N. Benson; Percutaneous Balloon Valvotomy in Pulmonary Atresia with Intact Ventricular Septum; Circulation, Aug. 19th 2003.

Henry W. Kort, David T. Balzer; Radiofrequency Perforation in the Treatment of Acquired left Pulmonary Artery Atresia Following Repair of Tetralogy of Fallot; Catheterization and Cardiovascular Interventions Sep. 2003;60(1):79-81.

Shyam S. Kothari, Sanjeev K. Sharma, Nitish Naik; Radiofrequency Perforation for Pulmonary Atresia and Intact Ventricular Septum; Indian Heart J Jan.-Feb. 2004;56(1):50-3 (Actual publication after Feb. 2004).

Daniel S. Levi, Juan C. Alejos, John W. Moore; Future of Interventional Cardiology in Pediatrics; Current Opinion in Cardiology Mar. 2003;18(2):79-90.

David G. Nykanen, Jaana Pihkala, Glenn P. Taylor, Lee N. Benson; Radiofrequency Assisted Perforation of the Atrial Septum in a Swine Model: Feasibility, Biophysical and Histological Characteristics; Circulation (Suppl 1) 100ppl-804 (Jan. 1999).

Carlos A.C. Pedra Luciano N.L. De Sousa, Simone R.F.F. Pedra, Waldinai P. Ferreira, Sergio L.N. Braga, Cesar A. Esteves, Maria Virginia T. Santana, J. Eduardo Sousa, Valmir F. Fontes; New Percutaneous Techniques for Perforating the Pulmonary Valve in Pulmonary Atresia with Intact Ventricular Septum; Arq Bras Cardiol. Nov. 2001;77(5):471-86.

Carlos A.C. Pedra, Ronaldo Mont 'Alverne Filho, Raul S. Arrieta, Ricardo Tellez, Valmir F. Fontes; Recanalization of a Discrete Atretic Right Pulmonary Artery Segment with a New Radiofrequency System; Catheterization and Cardiovascular Interventions Sep. 2003;60(1):82-7.

Baylis Medical Company Inc. "Radiofrequency Perforation System". Sep. 2001.

Gruschen R. Veldtman, Amanda Hartley, Naheed Visram, Lee N. Benson; Radiofrequency Applications in Congenital Hearth Disease; Expert Rev. Cardiovasc. Ther. Jan. 2004;2(1):117-26.

Gerd Hausdorf, Martin Schneider, Peter Lange; Catheter Creation of an Open Outflow Tract in Previously Atretic Right Ventricular Outflow Tract Associated with Ventricular Septal Defect; The American Journal of Cardiology, vol. 72 Aug. 1, 1993.

Christophe Fink, Mattias Peuster, Harald Bertram, Gerd Hausdorf; Transcatheter Recanalization of the Left Main Pulmonary Artery After Four Years of Complete Occlusion; Catheterization and Cardiovascular Interventions Jan. 2004;2(1):117-26.

G Hausdorf, I Schulze-Neick, Pe Lange; Radiofrequency-assisted "reconstruction" of the Right Ventricular Outflow Tract in Muscular Pulmonary Atresia with Ventricular Septal Defect; British Heart Journal, Apr. 1993;69(4):343-6.

\* cited by examiner

SURGICAL PERFORATION DEVICE WITH ELECTROCARDIOGRAM (ECG) MONITORING ABILITY AND METHOD OF USING ECG TO POSITION A SURGICAL PERFORATION DEVICE

TECHNICAL FIELD

The invention relates to a surgical perforation device with ECG monitoring ability and method of using ECG to position the surgical device. More specifically, the invention relates to a device and method for creating a controlled perforation in the atrial septum while using ECG to locate the fossa ovalis region on the atrial septum, and delivering a dilator and guiding sheath to the left atrium through the perforation over the surgical device.

BACKGROUND OF THE ART

Electrosurgical devices perforate or cut tissues when radio frequency (RF) electrical energy rapidly increases tissue temperature to the extent that the intracellular fluid becomes converted to steam, inducing cell lysis as a result of elevated pressure within the cell. The radio frequency range lies between 10 kHz and 300 MHz, but electrosurgical devices usually operate at a frequency between 400 kHz and 550 kHz. This technology can be used to create perforations in different types of tissue, such as heart tissue, vascular occlusions, and others. Commonly, RF devices are described for use in perforating vascular occlusions. A device to dilate and/or lance blood vessels that are morbidly contracted or clogged is described in a European Patent Application of Osypka, Publication Number EP 0315730, published May 15, 1989. This device describes the use of RF energy in either bipolar or monopolar application modes to open blood vessels by means of heat. Other devices intended to use RF energy to pass through occluded vessels have also been described (U.S. Pat. No. 5,364,393, of Auth et al., issued Nov. 15, 1994, WO 93/20747, publication of PCT Patent Application No. PCT/US93/03759, of Rosar, published Oct. 28, 1993, U.S. Pat. No. 5,098,431, of Rydell, issued Mar. 24, 1992, and U.S. Pat. No. 4,682,596 of Bales et al., issued Jul. 28, 1987). U.S. Pat. No. 6,293,945 B1, of Parins et al., issued Sep. 25, 2001 describes an electrosurgical instrument with suction capability. This device has three functions at the tip including cutting, coagulating, and suction. None of these devices however incorporate a means for verifying the location of the device within the body. One means for verifying location is described in U.S. Pat. No. 4,936,281, of Stasz, issued Jun. 26, 1990, which describes an ultrasonically enhanced RF catheter used for cutting. An ultrasonic transducer connected to an electronics module receives echo signals, enabling Doppler flow readings and ultrasound imaging of the vessel.

Having reliable information about the location of electrosurgical devices within a heart is an important aid to performing a successful procedure. It is often valuable to have more than one source of this information because every imaging technique has limitations, and using only one method can lead to erroneous information. A number of different tools and techniques have been used to assist the physician in locating devices within a heart. These include the use of fluoroscopy, cardiac pressure monitoring, transesophageal echocardiography, intracardiac echocardiography and the use of other devices in the heart to identify certain landmarks. L. J Jordaens et al. (2001) states that intracardiac echocardiography provides potentially useful information for electrophysiological studies and pacemaker implantation by visualization of important anatomical landmarks and structures.

Monitoring thy FCG tracings from an intracardiac surgical device can he a useful tool to verify the position of the device in a heart. An electrode with reference to a ground or a pair of electrodes placed directly on or in the heart will record a repeating pattern of changes in electrical action potential. Action potential can be defined as an explosion of electrical activity that is created by a depolarizing current within biological cells. As action potentials spread from the top chambers of the heart (atria) to the bottom chambers of the heart (ventricles), the voltage measure between a single electrode and a ground or a pair of electrodes will vary in a way that provides a picture or electrocardiogram (also referred to as electrograms), of the electrical activity of the heart. The nature of this picture can he varied by changing the position of the recording electrode(s); different locations in the heart are known to have characteristic ECG tracings or measurements. A bipolar recording is the voltage measurement between two electrodes and a unipolar recording is the voltage measurement between a single electrode and an electrode that is attached to a patient or an electrode that is built into a recorder or electrocardiograph and maintained at zero potential (ground). J. A Alvarez et al. (1991) who conducted experiments where ECG signals were monitored in a heart using a transseptal needle states that the endoatrial electrocardiogram registered while the needle (Brockenbrough transseptal needle) pressed muscular areas of the septum or the free atrial wall showed marked injury curves; on the other hand, no significant changes (in the endoatrial electrocardiogram) were observed at the area assumed to be the fossa ovalis floor. This implies that the ECG tracing observed when a surgical device is in contact with the fossa ovalis which is a membranous region will be markedly different from ECG tracing observed on the muscular areas of the atrial septum or the free atrial wall. This difference in tie electrocardiogram may be used to locate a surgical device on the region of the fossa ovalis in a heart.

Knowing the electrical action potential or ECG at the tip of a perforation device is a useful tool to determine the location of the device, particularly in instances where imaging techniques provide inconclusive information. A device that is used for monitoring and recording the electrical activity of the heart is described in U.S. Pat. No. 4,892,104, of Ito et al., issued Jan. 9, 1990; however the device is not capable of perforating tissue using RF energy. U.S. Pat. No. 6,296,615 B1, of Brockway et al., issued Oct. 2, 2001, describes a catheter with a physiological sensor. This catheter consists of a pressure transducer for monitoring pressure, as well as the ability to detect and/or transmit an electrical signal.

It is often required to create a perforation in the atrial septum to gain access to the left side of the heart interventionally to study or treat electrical or morphological abnormalities. It is also often desirable to create a hole in the septum in order to shunt the blood flow between the left and right sides of the heart to relieve high pressure or provide more blood flow to certain areas. The location on the atrial septum where a perforation is most commonly created is the fossa ovalis. The fossa ovalis is an oval depression in the inferior part of the interatrial septum. It represents the foramen ovale of the fetus and is generally a thin membraneous structure. Since the atrial septum is muscular in nature, it is generally easier to create a perforation across the fossa ovalis to gain access to the left side of a heart. Historically in these instances, a dilator and guiding sheath are introduced into the femoral vein over a guidewire and advanced into the right atrium. The guidewire, dilator and guiding sheath are usually packaged as a kit with the guiding sheath designed to track over the dilator. In most designs, the distal end of the dilator extends out beyond the distal end of the sheath once the two devices are locked together. Once the dilator and guiding sheath are positioned appropriately in the right atrium, a stiff needle such as the Transseptal needle of Cook Incorporated, Bloomington, Ind., USA is introduced through the dilator and guiding sheath set in the femoral vein and advanced through the vasculature into the right atrium. From there the needle tip is positioned at the fossa ovalis, the preferred location on the septum for creating a hole. Once in position, mechanical energy is used to advance the needle through the septum and into the left atrium. Once in the left atrium the needle can be attached to a pressure transducer and the operator can confirm a left atrial pressure before continuing with the procedure. An operator may dilate the hole by advancing the dilator over the needle into the left atrium and tracking the guiding sheath over the dilator and into the left atrium to provide access for other devices to the left heart once the needle and dilator are removed. As well, the operator may use another device such as a balloon catheter delivered over a guidewire to enlarge the hole made by the needle if a shunt between the right and left atria is desired.

Another device and method for creating a transseptal puncture is described in U.S. Pat. No. 5,403,338, of Milo, issued Apr. 4, 1995, which describes a punch that is intended to create an opening between two compartments. This device also makes use of mechanical energy, as with the transseptal needle.

These methods of creating a transseptal perforation rely on the skill of the operator and require practice to be performed successfully. The needles used in this procedure are very stiff and can damage the vessel walls as they are being advanced. In addition, the amount of force required to perforate the septum varies with each patient. If too much force is applied there is the possibility of perforating the septum and continuing to advance the needle so far that damage is done to other areas of the heart. C. R. Conti (1993) discusses this possibility, and states that if the operator is not careful, the posterior wall of the heart can be punctured by the needle when it crosses the atrial septum because of the proximity of the two structures. It can also be difficult to position the needle appropriately in hearts that have malformations, or an atypical orientation. Justino et al. (2001) note that despite improvements to the technique with the needle since its first introduction, most large studies continue to report failed or complicated mechanical transseptal punctures, for reasons such as unusual septal thickness, or contour. Patients with a muscular septum, as well as those with a thick septum can benefit from an alternative to the transseptal needle puncture (Benson et al, 2002), as it is difficult to control the amount of mechanical force required to create the puncture. Furthermore, children born with heart defects such as hypoplastic left heart syndrome could benefit from an alternative technique. The abnormal anatomy of these patients including a small left atrium increases the likelihood of injury or laceration of surrounding structures during transseptal puncture (Sarvaas, 2002). The patient population discussed above would benefit from a device and technique for transseptal perforation that allows for a more controlled method of perforation and a method to confirm that the perforation has been made in the correct location.

SUMMARY OF THE INVENTION

The present invention provides a surgical perforation device with ECG monitoring ability and method of using ECG to position the surgical device.

In accordance with a first aspect of the invention, there is provided a surgical device for cutting material and ECG monitoring ability. The surgical device comprises an elongate member having a distal region and a proximal region; an energy delivery device associated with the elongate member at the distal region for delivering cutting energy to the material, said energy delivery device adapted for connection to an energy source; and an ECG monitoring mechanism associated with the distal region for monitoring ECG about the distal region.

The cutting energy is at least one form of energy selected from a group consisting of: electrical current; microwave; ultrasound; and laser. When the energy is electrical current, the current may have a frequency within the radio frequency (RF) range. Further, when the material to be cut comprises cellular tissue, the energy delivery device is operable to deliver sufficient energy to the tissue to result in a rapid increase in the intracellular temperature causing vaporization of intracellular water and subsequent cell lysis.

In accordance with an embodiment of the first aspect, the ECG monitoring mechanism comprises at least one active electrode about the distal region; said ECG monitoring mechanism is adapted for connection to an ECG recorder such as an electrocardiograph. The ECG monitoring mechanism may be configured for operation in accordance with one or more of a unipolar mode and a bipolar mode. For example, a zero potential or ground electrode may be provided by an electrocardiograph coupled to the ECG monitoring mechanism to provide unipolar ECG recording. In accordance with another embodiment of the first aspect, the ECG monitoring mechanism may comprise two electrodes about the distal region and the electrodes may be configured in an arrangement where one of the electrodes is the measuring or active electrode and the second electrode is the reference or ground electrode. In a second option for a two or more electrode configuration, when the surgical device is used with at least one of a dilator and a sheath, the reference or ground electrode may be located at a distal region of at least one of the dilator and the sheath and the active electrode located about the distal region of the surgical device.

The energy delivery device may comprise a functional tip with at least one active electrode. Further the energy delivery device may comprise a functional tip having two or more electrodes and the electrodes may be configured in an arrangement where at least one of the electrodes is active and at least one is a return electrode.

In accordance with a further aspect of the invention, there is provided a method of surgery. The method comprises: (i) introducing a surgical device into a body of a patient, the surgical device comprising an elongate member having a distal region and a proximal region, an energy delivery device proximate to the distal region capable of cutting material and an ECG monitoring mechanism for measuring ECG proximate to the distal region; (ii) positioning the energy delivery device to a first desired location in the patient's body adjacent material to be cut using ECG signal monitoring as a guide; (iii) delivering energy using the energy delivery device to cut said material; and (iv) monitoring ECG in the heart using the ECG monitoring mechanism in order to determine the position of the surgical device. Steps (ii) and (iv) may be repeated, monitoring the ECG while positioning the device at a number of candidate locations in heart and locating the first desired location in the heart by the characteristic change in the ECG signal as the surgical device is moved against the first desired location.

The method may further comprise a step of (v) advancing the device to a second desired location. The method may comprise a step of: (vi) monitoring ECG using the ECG monitoring mechanism at the second location.

As a feature of this method aspect, step (i) comprises introducing the device into the patient's vasculature. The step of introducing the device into the patient's vasculature may comprise inserting the device into a dilator and a guiding sheath positioned in the patient's vasculature. The method may further comprise a step of (v) advancing the dilator and the sheath into the second location together over the spatially fixed surgical device or (v) advancing the dilator, sheath and surgical device all together into the second location.

In accordance with the method, the material may be tissue located on an atrial septum of a heart. Further, the region of tissue to be located using the ECG signals may be the fossa ovalis of a heart. In such a case, the ECG measured at the second location is the ECG measurement in the left atrium.

In another aspect of the invention, there is provided an electrosurgical device. The electrosurgical device comprises an elongate member having a distal region and a proximal region, said distal region insertable within and along a lumen within a body of a patient and maneuverable therethrough to a desired location where the device is operated to cut material and monitor ECG at the desired location; at least one electrode associated with the distal region for cutting tissue, said at least one electrode adapted for coupling to an electrical power source; and an ECG monitoring mechanism associated with the distal region for monitoring ECG to locate the desired location within the body, said mechanism adapted for coupling to an ECG recording system or electrocardiograph.

In a further aspect, there is provided a surgical device comprising means for cutting material at a desired location in a body of a patient; and means for determining a position of the device responsive to ECG signal change within the heart.

As a feature of this aspect, the device comprises a flexible elongate member having a proximal region and a distal region, the distal region is adapted for insertion within and along a lumen within the body and maneuverable therethrough to the desired location and the means for determining a position of the device is operable to determine the position of the distal region.

In accordance with yet another feature there is provided a method of cutting tissue at a desired location in a body of a patient. The method comprises: inserting a surgical device into the body, said surgical device comprising means for cutting material and means for determining a position of the device responsive to ECG signal change within the heart; and positioning said surgical device at the desired location in response to the means for determining a position of the device.

The method may comprise cutting material at the desired location and further comprise advancing the device in the body in response to said means for determining a position of the device. Optionally, the method comprises re-positioning said device for re-cutting in response to said means for determining a position of the device.

It is to be understood that references to cut or cutting material such as tissue in relation to the present invention may be defined as perforating, ablating, coagulating and any other mechanism to create a void.

BRIEF DESCRIPTION OF THE DRAWINGS

In order that the invention may be readily understood, embodiments of the invention are illustrated by way of examples in the accompanying drawings, in which.

It will be noted that throughout the appended drawings, like features are identified by like reference numerals.

DETAILED DESCRIPTION OF THE INVENTION

Figure 1:
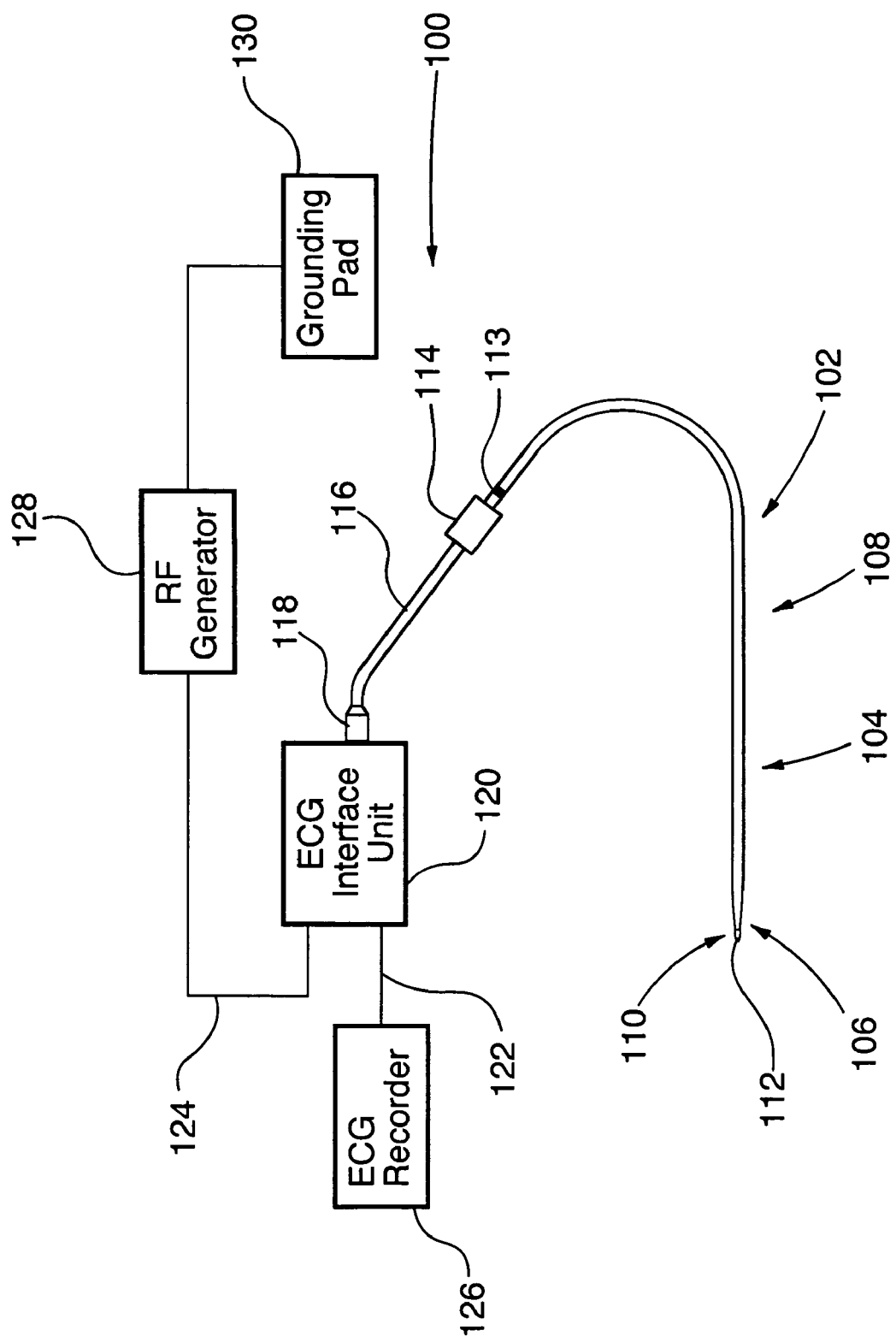
FIG. 1 illustrates a schematic view of an electrosurgical system including an electrosurgical device in accordance with an embodiment of the invention.

FIG. 1 illustrates an embodiment of an electrosurgical perforation device 102 in accordance with the invention in an electrosurgical system 100. Device 102 comprises an elongate member 104 having a distal region 106, and a proximal region 108. Distal region 106 is adapted to be inserted within and along a lumen of a body of a patient, such as a patient's vasculature, and maneuverable therethrough to a desired location proximate to material such as tissue to be cut.

The elongate member 104 is typically tubular in configuration, having at least one lumen 200 extending from proximal region 108 to distal region 106. Elongate member 104 is preferably constructed of a biocompatible polymer material that provides column strength to device 102. The elongate member 104 is sufficiently stiff to permit a dilator 710 and a soft guiding sheath 700 to be easily advanced over device 102 and through a perforation. Examples of suitable materials for the tubular portion of elongate member 104 are polyetheretherketone (PEEK), and polyimide. In a preferred embodiment, the outer diameter of the tubular portion of elongate member 104 tapers down to connect to distal region 106. In alternate embodiments the outer diameter of elongate member 104 and the outer diameter of distal region 106 are the same.

Distal region 106 is constructed of a softer polymer material so that it is pliable and atraumatic when advanced through vasculature. An example of a suitable plastic is Pebax (a registered trademark of Atofina Chemicals, Inc.). Distal region 106 preferably has a smaller outer diameter than elongate member 104 so that dilation of a perforation is limited while the distal region 106 is advanced through the perforation. Limiting dilation ensures that the perforation will not cause hemodynamic instability once device 102 is removed. The outer diameter of distal region 106 will preferably be no larger than 0.035" (0.897 mm). This is comparable to the distal outer diameter of the transseptal needle that is traditionally used for creating a perforation in the atrial septum. Elongate member 104 is preferably no larger than 0.050" (1.282 mm) which is also comparable to the transseptal needle dimensions.

Distal region 106 terminates at functional tip region 110 which comprises a device that functions as an energy delivery device as well as an ECG monitoring device. Functional tip region 110 comprises at least one active electrode 112 made of a conductive and radiopaque material, such as stainless steel, tungsten, platinum, or another metal. Optionally, one or more radiopaque markings (not shown) may be affixed to elongate member 104 to highlight the location of the transition from distal region 106 to elongate member 104, or other important landmarks on device 102. Alternately, the entire distal region 106 of device 102 may be radiopaque. This can be achieved by filling the polymer material, Pebax used to construct distal region 106 with a radiopaque filler. An example of a suitable radiopaque filler is Bismuth.

Proximal region 108 comprises a hub 114, a catheter connector cable 116, and a connector 118. As is known to persons of skill in the art, proximal region 108 may also have one or more depth markings 113 to indicate distances from functional tip region 110, or other important landmarks on device 102. Catheter connector cable 116 connects to ECG interface unit 120 via connector 118. ECG connector cable 122 connects ECG interface unit 120 to ECG recorder 126 which displays and captures ECG signals as a function of time. Generator connector cable 126 connects ECG interface unit 120 to an energy source such as Generator 128. ECG interface unit 120 functions as a splitter, permitting connection of electrosurgical device 102 to both ECG recorder 126 and RF generator 128. ECG signals can be continuously monitored and recorded and the filtering circuit (not shown) within ECG interface unit 120 permits RF energy to be delivered from RF generator 128 through electrosurgical device 102 without compromising the ECG recorder 126.

In an alternate embodiment (not shown), functional tip region 110 may comprise 2 or more active electrodes such as active electrode 112, where one active electrode is reserved for only energy delivery and one active electrode is reserved only for ECG monitoring. In such a design ECG interface unit 120 may not be required as there are two separate circuits in the electrosurgical device: one for carrying the RF energy and the other for ECG signals.

Generator 128 is preferably a radiofrequency (RF) electrical generator that is designed to work in a high impedance range. Because of the small size of active electrode 112 the impedance encountered during RF energy application is very high. General electrosurgical generators are typically not designed to deliver energy in these impedance ranges and thus not all RF generators can be used effectively with this device. Energy is preferably delivered as a continuous wave at a frequency between about 400 kHz and about 550 kHz. An appropriate commercially available generator for this application is the BMC RF Perforation Generator (model number RFP-100, Baylis Medical Company, Montreal, Canada). This generator delivers continuous RF energy at about 460 kHz. A grounding pad 130 is coupled to generator 128 for attaching to a patient to provide a return path for the RF energy when generator 128 is operating in a monopolar mode. Other embodiments could use pulsed or non-continuous RF energy. In still other embodiments of the electrosurgical perforation device 102, different energy sources may be used, such as microwave, ultrasound, and laser with appropriate energy delivery coupling devices and energy delivery devices.

Figure 2:
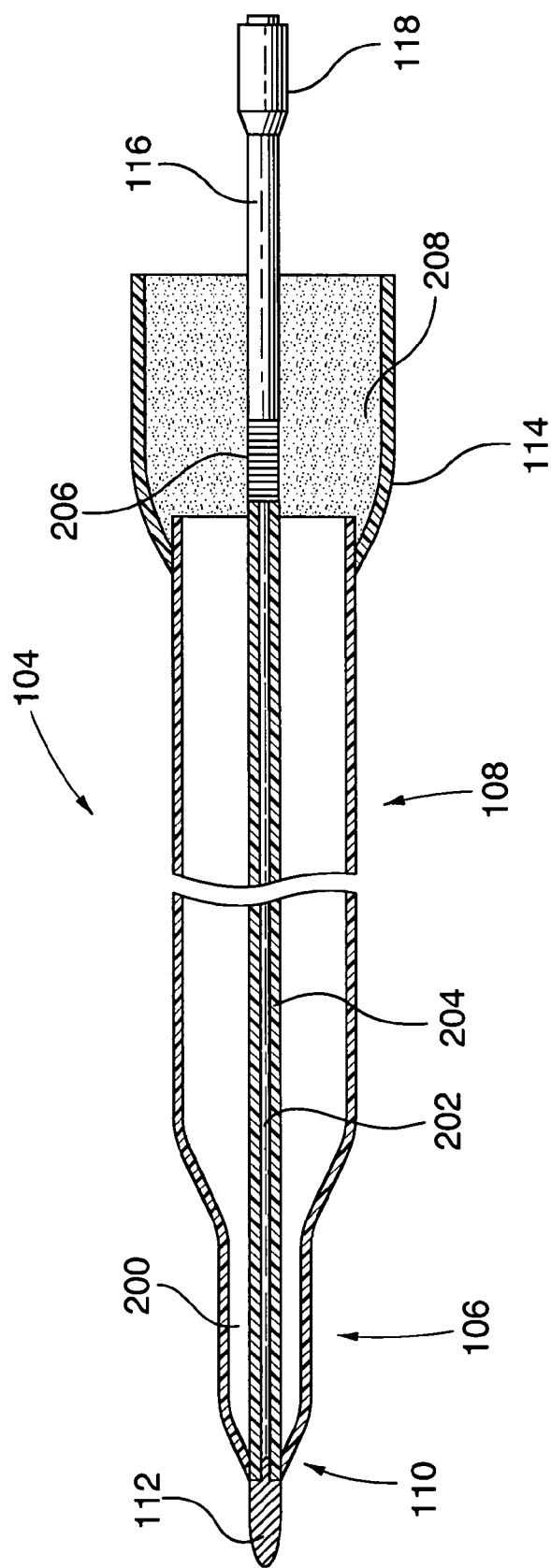
FIG. 2 illustrates a side cross-sectional view of the device of FIG. 1.

Referring to FIG. 2 a cross-section of device 102 is illustrated in accordance with the embodiment of FIG. 1. Functional tip region 110 comprises an active electrode 112 that is coupled to an insulated conducting wire 202. Conducting wire 202 is preferably attached to distal region 106 using an adhesive. Alternately, distal region 106 is melted onto insulation 204 on conducting wire 202 to form a bond.

Conducting wire 202 carries electrical energy from generator 128 to the active electrode 112. Conducting wire 202 also carries action potentials or voltage measured by active electrode 112 to ECG recorder 126. Action potentials or voltage measured by active electrode 112 is with reference to a zero potential or ground electrode (not shown) within ECG recorder 126 or a ground electrode (not shown) attached to a patient (not shown). Conducting wire 202 is covered with electrical insulation 204 made of a biocompatible material that is able to withstand high temperatures such as polytetrafluoroethylene (PTFE), or other insulating material. Conducting wire 202 preferably extends through a main lumen 200 of device 102 which lumen extends from proximal region 108 to distal region 106.

Figure 3:
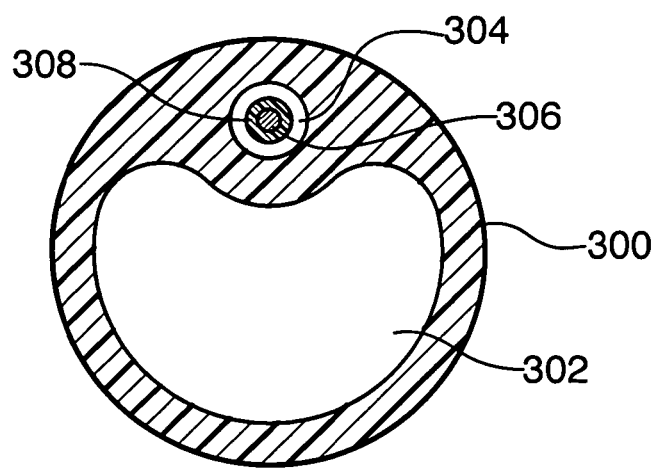
FIG. 3 illustrates a cross-sectional view of an alternate embodiment of the device.

In an alternate embodiment shown in cross section view in FIG. 3, an elongate member 300 comprises main lumen 302 and a separate lumen 304. The separate lumen 304 contains a conducting wire 306 covered with electrical insulation 308 therein and main lumen 302 can be used, for example, for aspiration of blood, injection of contrast or other media, among other purposes. Optionally, main lumen 302 which extends between proximal and distal regions of elongate member 300 provides a pressure sensing mechanism to be used for monitoring blood pressure. As is known to persons of skill in the art, main lumen 302 may be coupled to a pressure transducer, preferably external to device 102, to produce a signal that varies as a function of pressure sensed as the surgical device is positioned in and about a body. The pressure transducer may be electrically coupled to a pressure monitoring system (not shown) that converts the transducer's signal and displays a pressure contour as a function of time. Pressure monitoring may be useful in locating a surgical device within a body.

In the embodiment of FIG. 2, main lumen 200 extends from proximal region 108 along elongate member 104 and through distal region 106 of device 102.

At proximal region 108, conducting wire 202 is electrically coupled to catheter connector cable 116 within hub 114 by an electrical joint 206. This joint can be made by soldering, or another wire joining method known to people of ordinary skill in the art. Catheter connector cable 116 terminates with a connector 118 that can mate with either the ECG interface unit 120, or a separate extension connector cable (not shown). Catheter Connector cable 116 and connector 118 are made of materials suitable for sterilization, and will insulate the user from energy traveling through the conductor.

A hub 114 surrounds electrical joint 206 and proximal end of elongate member 104 in order to conceal these connections. The hub 114 is made of a polymeric material, and is filled with a filling agent 208 such as an epoxy, or another polymeric material in order to hold catheter connector cable 116 in place.

Figure 4:
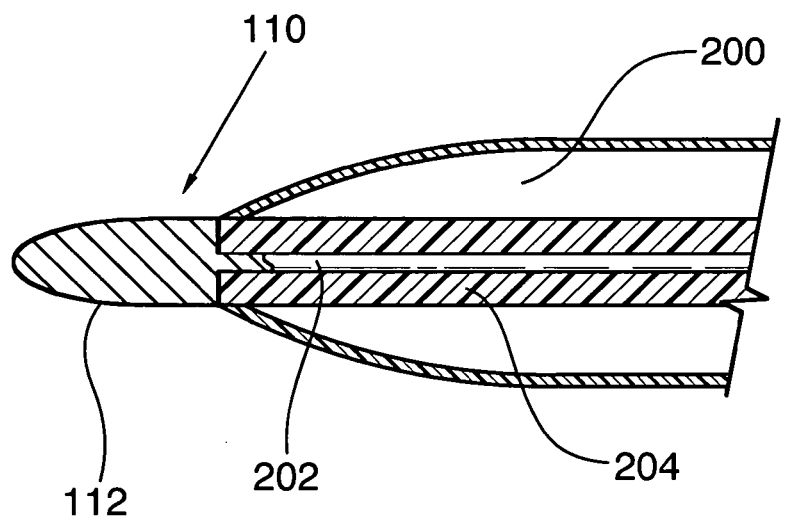
FIG. 4 illustrates an active electrode of the device of FIG. 1.

Referring to FIG. 4 there is illustrated a side cross-sectional view of a preferred embodiment of functional tip region 110. Functional tip region 110 comprises one active electrode 112 configured in a bullet shape. Active electrode 112 is preferably 0.059" (0.15 cm) long and preferably has an outer diameter of 0.016" (0.04 cm). Active electrode 112 is coupled to an end of conducting wire 202, also made out of a conductive and radiopaque material. RF energy is delivered through active electrode 112 to tissue, and travels through the patient to grounding pad 130, which is connected to generator 128. Additionally, action potentials or voltage measured from tissue through active electrode 112 travel through conducting wire 202 to ECG recorder 126. Alternate embodiments of active electrode 112 are configured in shapes other than a bullet. These shapes include a spherical shape, a rounded shape, a ring shape, a semi-annular shape, an ellipsoid shape, an arrowhead shape, a spring shape, and a cylindrical shape, among others.

Figure 5:
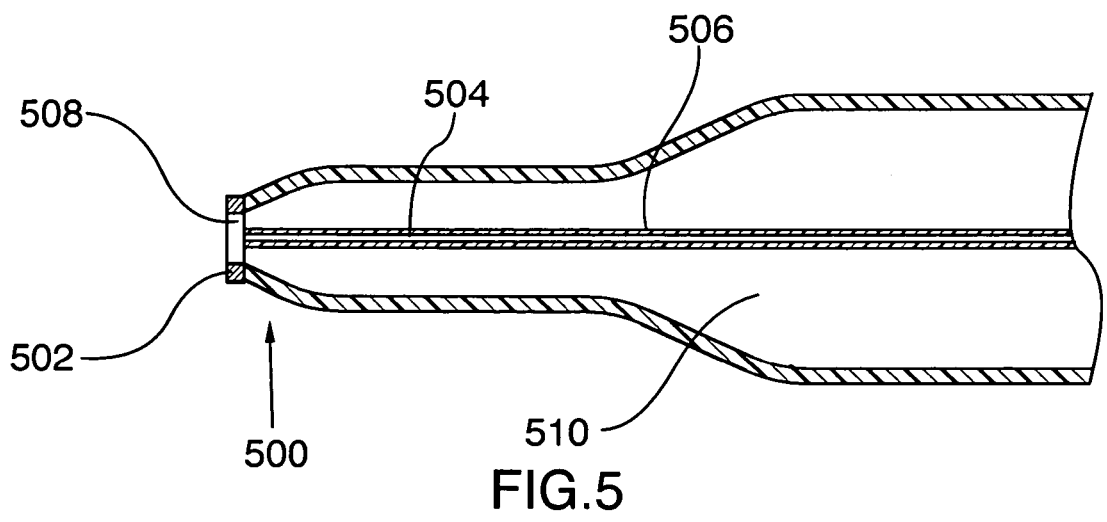
FIG. 5 illustrates an alternate embodiment of the distal region of a device in accordance with the invention.

Referring to FIG. 5 there is illustrated an alternate embodiment of a functional tip region 500. Functional tip region 500 comprises one active electrode 502 in a ring configuration. Conducting wire 504 covered with electrical insulation 506 is coupled to the active electrode 502, and active electrode 502 is positioned around a perimeter of a single opening 508 that provides a pathway between main lumen 510 and a patient's body. Another similar embodiment to functional tip region 500 comprises an active electrode in a partially annular shape (not shown). In other embodiments (not shown), a functional tip comprises multiple electrodes. Such electrodes may operate in a monopolar mode as with the embodiments detailed in FIGS. 2 and 5. Such electrodes may be arranged in a manner such that at least one electrode may be located distally to all the other electrodes.

Figure 6:
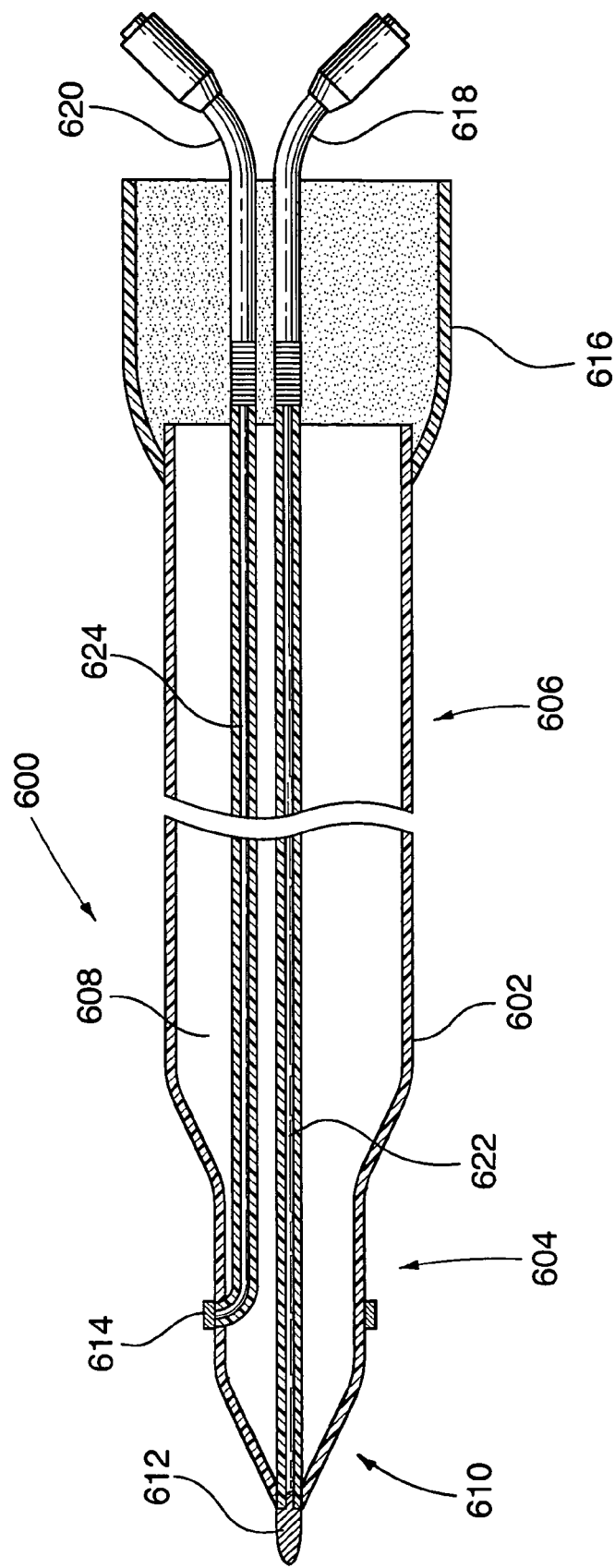
FIG. 6 illustrates a side cross-sectional view of an alternate embodiment of the device.

Referring to FIG. 6, there is illustrated a side cross-sectional view of an alternate embodiment of device 600 which operates in a bipolar mode. Device 600 comprises an elongate member 602 having a distal region 604, and a proximal region 606. Elongate member 602 has at least one lumen 608 extending from proximal region 606 to distal region 604. The outer diameter of elongate member 602 tapers down to connect to distal region 604. In alternate embodiments the outer diameter of elongate member 602 and the outer diameter of distal region 604 are the same.

Figures 7A, 7B:
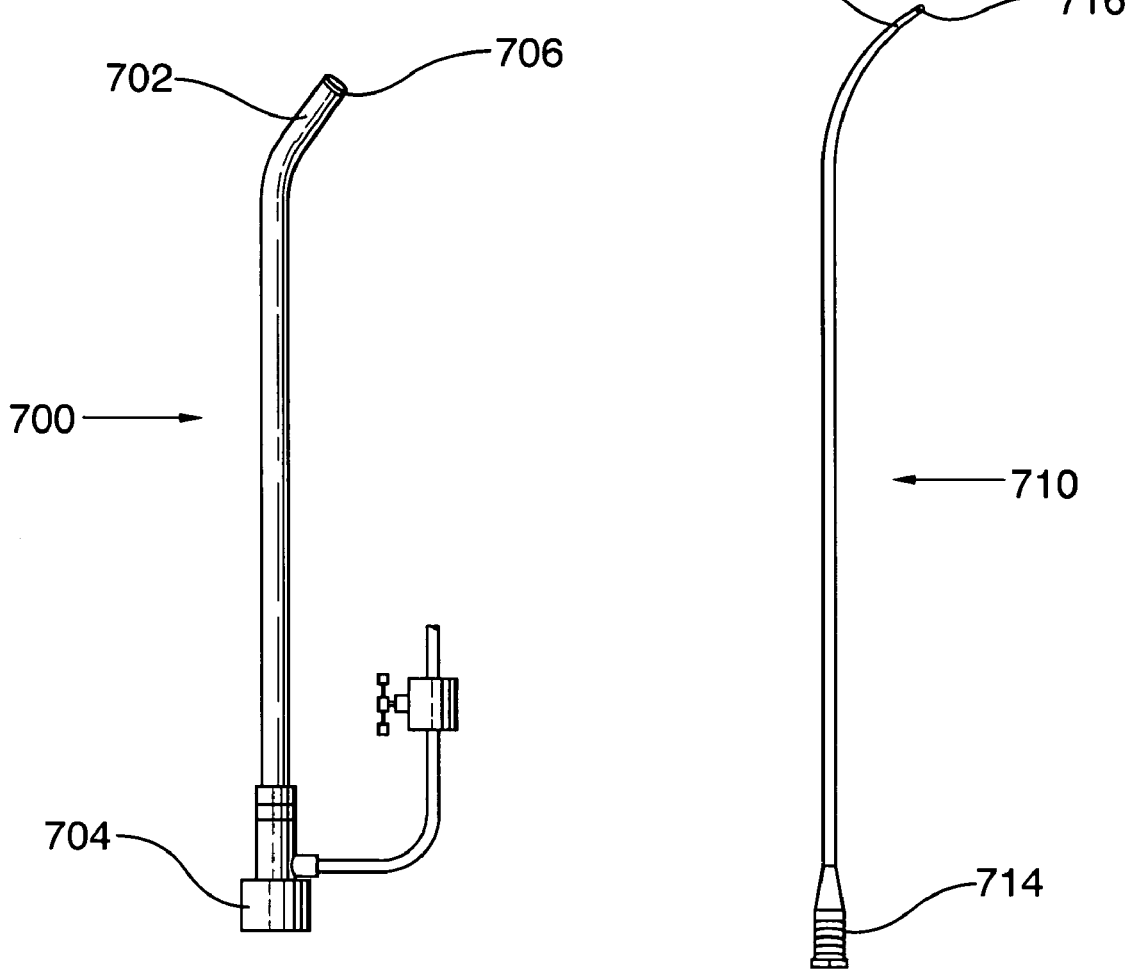
FIGS. 7A and 7B illustrate a side view of a guiding sheath and a dilator respectively.

Distal region 604 terminates at functional tip region 610. Functional tip region 610 comprises one active electrode 612 and one reference electrode 614. Reference electrode 614 is located proximally to active electrode 612 on functional tip region 610. With reference to FIGS. 7A and 7B, in alternate embodiments, a reference electrode 716 may be located at a distal tip 712 of a dilator 710 or a reference electrode 706 may be located at a distal tip 702 of a sheath 700. Both the active electrode 612 and reference electrode 614 can be configured in many different shapes. These shapes include a spherical shape, a rounded shape, a ring shape, a semi-annular shape, an ellipsoid shape, an arrowhead shape, a spring shape, and a cylindrical shape, among others.

Proximal region 606 comprises a hub 616, an active connector cable 618, and a reference connector cable 620. Both active connector cable 618 and reference connector cable 620 connect to ECG interface unit (not shown).

Active electrode 612 is coupled to an insulated conducting wire 622. Conducting wire 622 carries electrical energy from a generator (not shown) to the active electrode 612. Conducting wire 622 also carries action potentials or voltage measured by active electrode 612 to an ECG recorder (not shown). Conducting wire 622 extends through main lumen 608 of device 600. Conducting wire 622 extends along elongate member 602 from distal region 604 to proximal region 606 and is electrically coupled to active connector cable 618 within hub 616.

Reference electrode 614 is coupled to an insulated conducting wire 624. Conducting wire 624 carries electrical energy from a patient (not shown) to a generator (not shown). Conducting wire 624 also carries action potentials or voltage measured by reference electrode 614 to an ECG recorder (not shown). Conducting wire 624 extends through main lumen 608 of device 600. Conducting wire 624 extends along elongate member 602 from distal region 604 to proximal region 606 and is electrically coupled to reference connector cable 620 within hub 616.

In the bipolar mode, RF energy is delivered through active electrode 612, and returns to the generator through reference electrode 614. The use of an active electrode 612 of surgical device 600 and a reference electrode 614 of device 600, or alternatively at least one of reference electrode 706 of sheath 700 and reference electrode 716 of dilator 710, eliminates the need for a grounding pad to be attached to the patient as is well understood by persons of ordinary skill in the art. With an active-return electrode arrangement at or about functional tip region 610, action potentials or voltage measured by the active electrode 612 are with reference to the ground or reference electrode 614 located at the function tip region 610 or about the tip region 610 when at least one of the reference electrode 706 of sheath 700 and reference electrode 716 of dilator 710 is used. The ECG recorder assigns a zero potential value to the reference electrode 614, eliminating the need for a zero potential or ground electrode within the ECG recorder or on a patient. Higher fidelity recording may be achieved using a configuration with the return electrode at or about functional tip region 610.

ECG recorder 122 is connected to device 102 through the ECG interface unit 120. Hub 114 is coupled to catheter connector cable 116 that is coupled to connector 118 as shown in FIG. 1. Connector 118 is attached to ECG Interface unit 120. When device 102 is maneuvered in a heart, electrical action potentials or voltage detected by active electrode 112 are transmitted along conducting wire 202 and catheter connector cable 116, through ECG interface unit 120 and are captured and displayed on a display device (not shown) of ECG recorder 126. Different locations in a heart are at different potentials and the voltage measured varies as the position of active electrode 122 is varied. A conversion circuit (not shown) preferably within ECG recorder 126 converts the measured voltage or potential into a picture or waveform recording that varies as a function of time.

Device 102 can be used for general electrosurgery in instances where it is desirable to cut tissue or other material and simultaneously monitor ECG. More specifically, it can be used for creating a perforation such as a transseptal perforation. As is known to persons of skill in the art, the frequency ranges for electrosurgery and ECG monitoring are different. Electrical filtering circuits may be used within the system to permit simultaneous delivery of RF energy and monitoring of ECG signals without electrical interference or compromise. In order to create a perforation in the heart, device 102 is delivered to the heart using a guiding sheath and dilator known to those of ordinary skill in the art. FIGS. 7A and 7B show embodiments of guiding sheath 700 and dilator 710. Guiding sheath 700 has a tip 702 at the distal end and a proximal hub 704. Optionally, guiding sheath 700 may have a reference electrode 706 located at distal tip 702. As is known to persons of skill in the art, reference electrode 706 may be located anywhere along guiding sheath 700 and may be configured in many different shapes. Guiding sheath 700 has a lumen (not shown) through which dilator 710 is most commonly delivered. Dilator 710 has a tip 712 at the distal end and a proximal hub 714. Optionally, dilator 710 may have a reference electrode 716 located at distal tip 712. Dilator 710 has a lumen (not shown) through which a guidewire (not shown) or electrosurgical perforation device 102 can be delivered.

Figure 8:
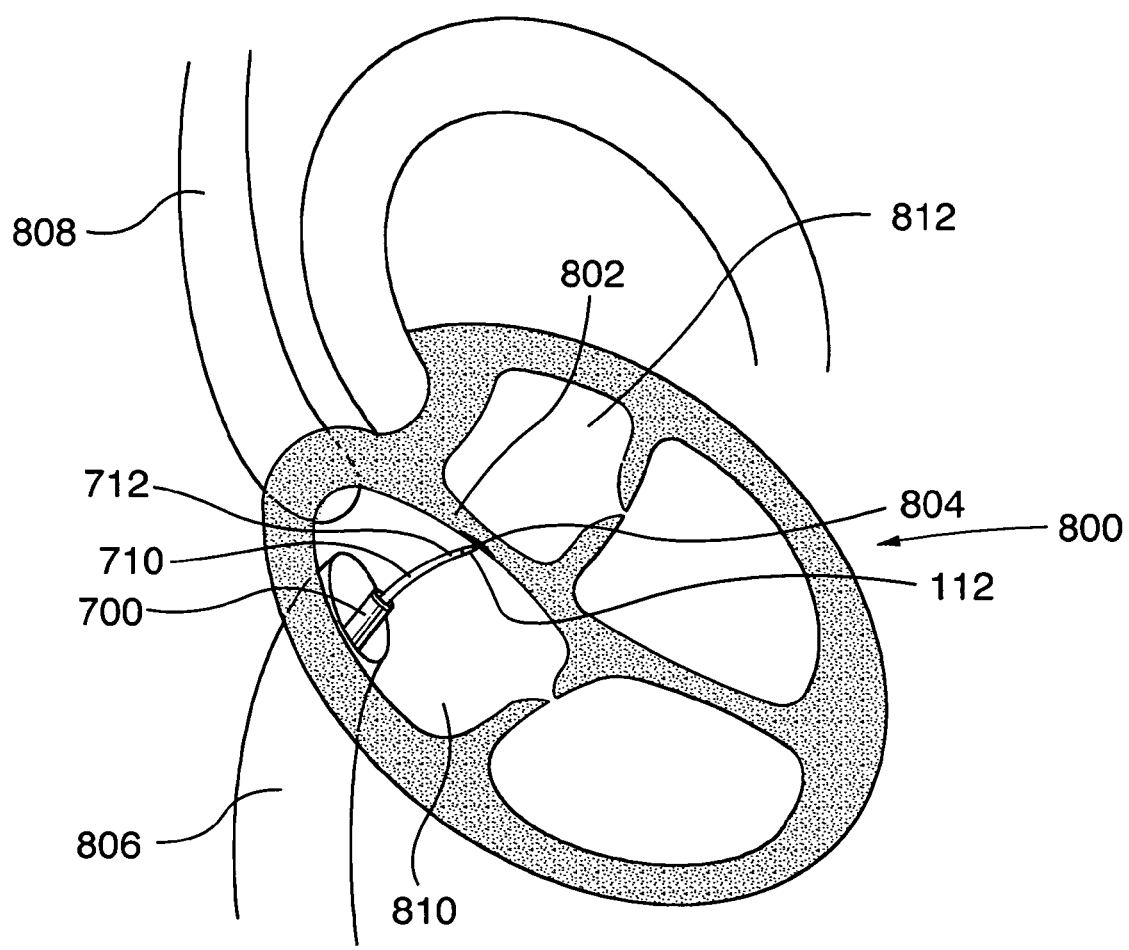
FIG. 8 illustrates the position of the device of FIG. 1 against an atrial septum of a heart.

Referring to FIG. 8 there is illustrated electrosurgical perforation device 102 inserted through a dilator 710 and sheath 700 within a heart 800 of a patient. Operations 900 for an embodiment of a method for creating a transseptal perforation is outlined in flow chart form in FIGS. 9A and 9B. In accordance with this method aspect, to deliver the tip 712 of the dilator 710 against the fossa ovalis 804 (step 902) a guiding sheath 700 and dilator 710 with a lumen larger than the outer diameter of the electrosurgical perforation device 102 is introduced into a patient's vasculature. Access is gained to the femoral vein of the patient (not shown). Guiding sheath 700 and dilator 710, known to those of ordinary skill in the art, are advanced together through the vasculature over a guidewire (not shown), approaching the heart from the Inferior Vena Cava 806, into the Superior Vena Cava (SVC) 808 of the heart 800. The guidewire (not shown) is withdrawn from the patient. The sheath 700 and dilator 710 are withdrawn from the SVC 808, into a right atrium 810. Contrast agent is delivered through dilator 710 while positioning the dilator 710 and sheath 700 along an atrial septum 802. The sheath 700 and dilator 710 are now positioned within the right atrium 810 of heart 800 so that the tip 712 of dilator 710 is located against the upper region of the atrial septum 802 (step 902).

Once the tip 712 of dilator 710 is in position against the upper region of the atrial septum 802, device 102 can be advanced through the dilator 710 until functional tip region 110 is located distally to tip 712 of dilator 710 (step 904). Device 102 is coupled to the ECG recorder 126 and an ECG signal is monitored through active electrode 112 providing an ECG tracing, known to those of ordinary skill in the art, may be shown on ECG recorder 126. A technique for obtaining an ECG tracing was previously described. Device 102, dilator 710, and guiding sheath 700 are now dragged along the atrial septum 802 while monitoring the ECG tracing on the ECG recorder 126 (step 906). Confirmation of position of active electrode 112 of device 102 against the fossa ovalis 804 is made once a distinctive change in the ECG tracing on ECG recorder 126 is observed. This is due to active electrode 112 advancing over the region of the fossa ovalis 804 which is membranous in comparison with the muscular atrial septum 802. J. A. Alvarez et al. (1991) who performed experiments on the usefulness of the intra-cavitary electrocardiogram ECG (ECG recorded using a transseptal needle) in the localization of the fossa ovalis states that when the tip of the needle was laid against the fossa ovalis floor, the endoatrial electrocardiogram registered a slight or no injury curve, even when the pressure was sufficient to perforate the septum. On the contrary, the pressure on any other areas of the muscular septum or atrial walls elicited a bizarre monophasic injury curve. This shows that the ECG signal recorded by a surgical device while on the membranous fossa ovalis will be damped in comparison with the ECG signal recorded on the muscular areas of the atrial septum or atrial walls. This difference in ECG signal may be useful in locating the region of the fossa ovalis as a surgical device is positioned within a heart. ECG may be observed on a screen (not shown) and printed on a chart (not shown) for example. The distinctive change may be signaled for observation as well using an alarm such as a sound or light signal.

Figure 9A:
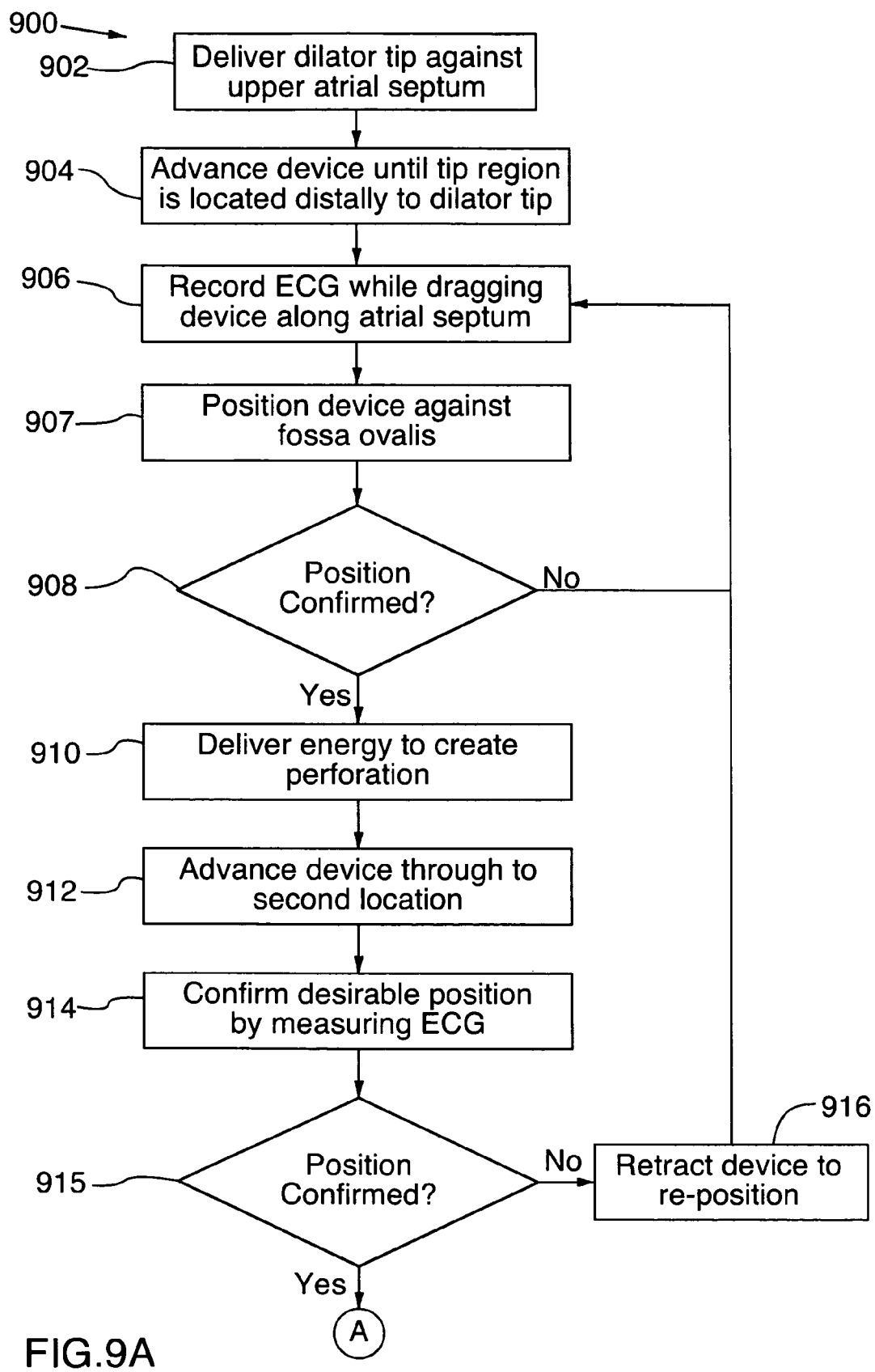
FIGS. 9A and 9B illustrate a flow chart of operation of a transseptal perforation method in accordance with an embodiment of the invention.
Figure 9B:
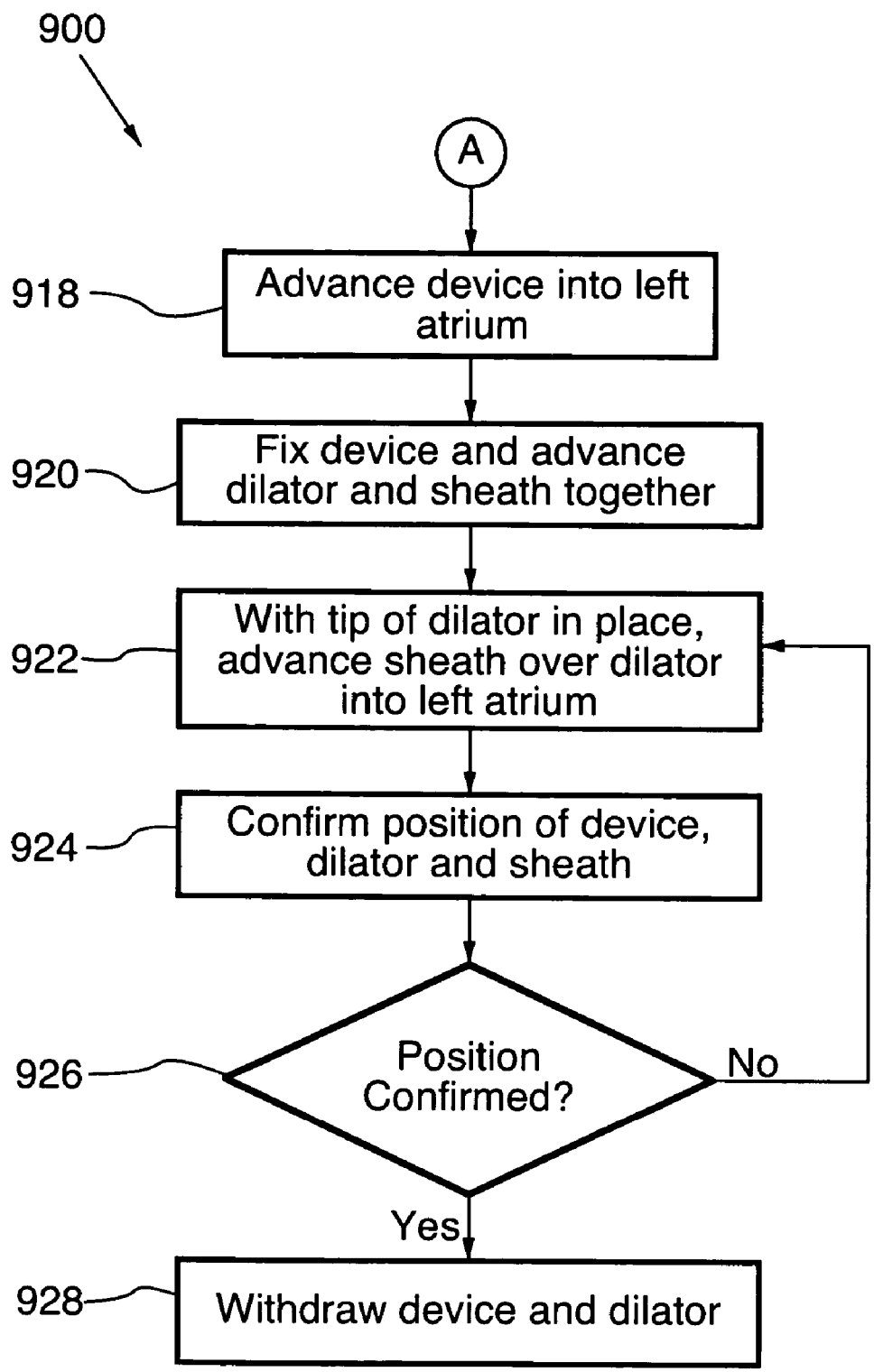

Functional tip region 110 is now directed toward the fossa ovalis 804, a first desired location on the atrial septum 802 to create a perforation (FIG. 8 and step 907 of FIG. 9A).

The position of functional tip region 110 and active electrode 112 may be additionally confirmed using an imaging modality such as fluoroscopy or intracardiac echocardiography. The position is evaluated and if the desired position is not confirmed (step 908, No branch), step 906 may be repeated. If confirmed (step 908, Yes branch), energy may be delivered to create the perforation. For example, generator 128 is activated and RF energy is delivered through device 102 to make a perforation (step 910).

The functional tip region 110 of device 102 is thereafter advanced through the perforation and into a second location (step 912). Advancement may be monitored under fluoroscopy, for example, using the radiopaque markings (not shown) on the distal region 106 of device 102. The preferred second location is left atrium 812 of the heart. The distal region 106 of device 102 is advanced incrementally into the left atrium 812 through dilator 704, for example, in 1 cm (about 0.39") increments. When the distal region 106 of device 102 is believed to be located in the left atrium 812, the evaluation of the ECG tracing (step 914) can be performed for confirmation. Device 102 remains coupled to ECG recorder 126 so that an ECG tracing at the second location can be monitored.

After successful perforation, a left atrial ECG tracing, known to those of ordinary skill in the art, will be shown on the ECG' recorder 126. In the event that the imaging and ECG tracings show that the perforation is made in an undesirable location (step 915, No branch), device 102 is retracted into the right atrium 810 (step 916) and is repositioned for another perforation attempt (step 906). If the perforation is successfully made in the correct location (step 915, Yes branch), distal region 106 of device 102 is preferably further advanced through the perforation. When device 102 is fully inserted into the dilator 710, hub 114 of the device 102 will be flush against proximal hub 714 of dilator 710 (step 918, FIG. 9B). When fully inserted, device 102 provides sufficient support to permit the dilator 710 to be advanced over it through the perforation.

Hub 114 of device 102 may be fixed in place spatially, and both the proximal hub 714 of dilator 710 and proximal hub 704 of sheath 700 are incrementally advanced, together, thus sliding the dilator 710 and sheath 700 over device 102 (step 920). The tip 712 of dilator 710 and the tip 702 of sheath 700 may be monitored under fluoroscopy as they are advanced over device 102 and once the tip 712 of dilator 710 has breeched the perforation, and advanced into the left atrium 812, the tip 702 of sheath 700 is advanced over dilator 710, across the perforation and into the left atrium 812 (step 922).

In an alternate method of advancing the sheath and dilator into the left atrium, (not shown), once distal region 106 is fully advanced through the perforation and into the left atrium 812, and hub 114 of device 102 is flush against proximal hub 714 of dilator 710, hub 114 of device 102 and proximal hub 714 of dilator 710 and proximal hub 702 of sheath 700 may all be advanced together. Advancement may be performed under monitoring by fluoroscopy. Forward momentum will cause the tip 712 of dilator 710 to breech the perforation, advancing into the left atrium 812. The tip 702 of sheath 700 will follow over dilator 710, across the perforation and into the left atrium 812.

At step 924, the positions of distal region 106 of device 102, tip 712 of dilator 710 and tip 702 of sheath 700 are confirmed, for example, under fluoroscopy to be in the left atrium 812. If not in the desired location (step 926), step 920 may be repeated. If the positions are confirmed (step 926), device 102 and dilator 710 may now be respectively withdrawn outside the body, preferably under fluoroscopic guidance (step 928). While maintaining the position of tip 712 of dilator 710 and tip 702 of sheath 700 in the left atrium 812, device 102 may be withdrawn. Dilator 710 may now be withdrawn outside the body under fluoroscopic guidance, while maintaining the position of the tip 702 of sheath 700 in the left atrium 812. Optionally, a contrast agent may now be injected through sheath 700 into the left atrium 812, or blood aspirated through sheath 700 from the left atrium 812 and sheath 700 may now be used to deliver other catheters (not shown) to the left atrium 812.

The present invention in various aspects thus provides a device and method that is capable of creating a controlled perforation while determining a position of the device in response to action potentials or measured voltage at a location in the heart. In addition, the present invention provides a method for delivering a dilator and sheath over the device after the perforation. The controlled perforation is created by the application of energy by a generator to a functional tip on the device. A method for determining the position of the device may comprise monitoring action potentials or measured voltage through an active electrode in a unipolar or bipolar manner and displaying the ECG tracings on an ECG recorder. In this embodiment there is at least one active electrode at the functional tip region for monitoring action potentials which are captured and displayed as ECG tracings on an ECG recorder.

The device of the invention is useful as a substitute for a traditional transseptal needle to create a transseptal perforation. The device of the present invention preferably has a soft distal region with a functional tip that uses RF energy to create a perforation across a septum, making the procedure more easily controlled and less operator dependent than a transseptal needle procedure. The soft distal region of the device reduces incidents of vascular trauma as the device is advanced through the vasculature. The application of RF energy is controlled via an electric generator, eliminating the need for the operator to subjectively manage the amount of force necessary to cross the septum with a traditional needle. The present invention eliminates the danger of applying too much mechanical force and injuring the posterior wall of the heart.

The present invention also provides a method for the creation of a perforation in an atrial septum. ECG monitoring is particularly advantageous in this procedure, as there is the possibility of inadvertently perforating the aorta due to its proximity to the atrial septum. Electrical action potential or voltage measurements displayed as ECG tracings allow the operator to confirm that the distal end of the device has entered the left atrium, and not the aorta, or another undesirable location in the heart. Preferably, the device will also be visible using standard imaging techniques; however the ability to monitor ECG provides the operator with a level of safety and confidence that would not exist using only standard imaging techniques.

The present invention also provides a method for delivering the dilator and sheath over the electrosurgical perforation device into the left atrium once a successful perforation has been created. One of the main reasons for creating a transseptal perforation is to gain access to the left side of the heart for delivery of catheters or devices to treat left-sided heart arrhythmias or defects.

While the surgical device thus described is capable of cutting living tissue, it will be understood by persons of ordinary skill in the art that an appropriate device in accordance with the invention will be capable of cutting or removing material such as plaque or thrombotic occlusions from diseased vessels as well.

Although the above description relates to specific embodiments as presently contemplated by the inventors, it is understood that the invention in its broad aspect includes mechanical and functional equivalents of the elements described herein.

What is claimed is:

1. A method for creating a channel through a cardiac septal material located in a body of a patient, said body having a body vasculature, said method using a surgical device comprising a substantially elongated member, said elongated member defining a proximal region and a longitudinally opposed distal region, said surgical device also comprising an active electrode for delivering a radio-frequency electrical current into said cardiac septal material, said active electrode being operatively coupled to said elongated member substantially adjacent said distal region, said method further using a grounding pad attachable to said patient for providing a return path for said radio-frequency electrical current, said method comprising:

introducing said surgical device into said body of said patient;

attaching said grounding pad to said patient;

positioning said active electrode at a first desired location in said body of said patient, said first desired location being substantially adjacent said cardiac septal material;

obtaining data about an electrical parameter of said cardiac septal material using said active electrode so as to substantially assess the position of said surgical device; and creating said channel through said cardiac septal material by delivering said radio-frequency electrical current from said active electrode to said grounding pad, said radio-frequency electrical current being delivered through said cardiac septal material;

wherein said active electrode has a diameter of 0.04 cm or less.

2. The method as claimed in claim 1, further comprising advancing said active electrode through said channel and out of said cardiac septal material to a second desired location.

3. The method as claimed in claim 2 further comprising obtaining data about an electrical parameter of said cardiac septal material so as to substantially assess the position of said surgical device after advancing said active electrode.

4. The method as claimed in claim 1 wherein introducing said surgical device comprises introducing said surgical device into said body vasculature.

5. The method as claimed in claim 4 wherein introducing said surgical device into said body of said patient comprises inserting said surgical device into a dilator and a guiding sheath positioned in said body vasculature.

6. The method as claimed in claim 5 comprising maintaining said surgical device substantially fixed relatively to said cardiac septal material and advancing said dilator and said sheath over said surgical device through said channel.

7. The method as claimed in claim 5 comprising advancing substantially jointly said dilator, said sheath and said surgical device through said channel.

8. The method as claimed in claim 1, comprising advancing said dilator, said sheath and said surgical device together through said channel.

9. The method as claimed in claim 1, wherein said active electrode has a diameter of 0.04 cm.

10. The method as claimed in claim 1 wherein positioning said active electrode includes moving said active electrode relative to said cardiac septal material while monitoring said data about said electrical parameter of said cardiac septal material so as to substantially assess the position of said active electrode.

11. The method as claimed in claim 10 wherein the first desired location is determined in response to the observation of a distinctive change in said electrical parameter of said cardiac septal material.

12. The method as claimed in claim 11 wherein said electrical parameter of said cardiac septal material includes a voltage measured on said cardiac septal material, said first desired location being identified by a reduction in said voltage measured on said cardiac septal material.

13. The method as claimed in claim 11 wherein the first desired location is a fossa ovalis of the heart.

* * * * *